United States Patent
Van Osselaer et al.

(10) Patent No.: US 6,858,758 B2
(45) Date of Patent: Feb. 22, 2005

(54) METHOD FOR PRODUCING BISPHENOLS

(75) Inventors: Tony Van Osselaer, Krefeld (DE); Werner Verhoeven, Kalmthout (BE); Domien Sluyts, Hoevenen (BE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/196,868

(22) Filed: Jul. 16, 2002

(65) Prior Publication Data

US 2003/0050514 A1 Mar. 13, 2003

(30) Foreign Application Priority Data

Jul. 18, 2001 (DE) ........................................ 101 350 012

(51) Int. Cl.$^7$ .............................................. C07C 39/16
(52) U.S. Cl. ...................................... 568/728; 568/727
(58) Field of Search ................................ 568/727, 728

(56) References Cited

U.S. PATENT DOCUMENTS

| | | | | |
|---|---|---|---|---|
| 2,359,242 A | * | 9/1944 | Perkins | |
| 2,730,552 A | * | 1/1956 | Williamson | |
| 2,730,553 A | * | 1/1956 | Williamson | |
| 2,775,620 A | * | 12/1956 | Williamson | |
| 5,210,328 A | | 5/1993 | Freitag et al. | ............... 568/721 |
| 5,336,812 A | | 8/1994 | Salek et al. | ................. 568/721 |
| 6,284,931 B1 | | 9/2001 | Isota et al. | .................. 568/721 |

* cited by examiner

*Primary Examiner*—Michael L. Shippen
(74) *Attorney, Agent, or Firm*—Joseph C. Gil; Aron Preis

(57) ABSTRACT

A method for producing a bisphenol is disclosed. The method entails reacting in at least one first reactant selected from a first group consisting of phenol and substituted phenols with at least one second reactant selected from a second group consisting of ketones and diols, in the presence of hydrogen chloride catalyst and volatile sulphur compound having an SH bond as co-catalyst. The reaction product is a mixture that contains bisphenol, first reactant and second reactant. The catalyst and co-catalyst and water of reaction are separated by distillation. The method is characterized by the high reaction rates and selectivities.

7 Claims, No Drawings

METHOD FOR PRODUCING BISPHENOLS

FIELD OF THE INVENTION

The invention relates to bisphenols and more particularly to a method for their production.

SUMMARY OF THE INVENTION

A method for producing a bisphenol is disclosed. The method entails reacting in at least one first reactant selected from a first group consisting of phenol and substituted phenols with at least one second reactant selected from a second group consisting of ketones and diols, in the presence of hydrogen chloride catalyst and volatile sulphur compound having an SH bond as co-catalyst. The reaction product is a mixture that contains bisphenol, first reactant and second reactant. The catalyst and co-catalyst and water of reaction are separated by distillation. The high reaction rates and selectivities characterize the method.

BACKGROUND OF THE INVENTION

Bisphenols are raw materials for the production of polycondensation materials such as epoxy molding compounds, polyether sulphones, polyether ketones or polycarbonates. Bisphenols are generally produced by reacting phenol or substituted derivatives thereof with suitable ketones in the presence of acidic catalyst and with separation of water. The industrially most significant bisphenol is bisphenol A (BPA), produced from phenol and acetone. Bisphenols derived from cyclic alkanes, for example the condensation product of phenol and 3,3,5-trimethylcylohexanone (BP-TMC) are also very important in the production of polycarbonates.

Homogeneously dissolved acids such as hydrogen chloride or heterogeneous acid fixed-bed catalysts such as sulphonated cross-linked polystyrene resins (acid ion exchangers) are used as catalysts for the production of bisphenols. While the use of heterogeneous catalysts is to be preferred from certain viewpoints to the use of homogeneous catalysts, it may be found in EP-A 995 737 that inadequate reaction and selectivity is achieved with this type of catalyst for certain ketones. Therefore, the use of strong acids such as hydrochloric acid as a catalyst is to be preferred for a large number of ketones, in particular cyclic ketones. To further increase the ketone reaction and to raise the selectivity of the reaction, sulphur-containing organic compounds such as alkyl mercaptans, thiocarboxylic acids or dialkylsulphides, as described in U.S. Pat. No. 5,210,328, are used as cocatalysts. The use of specific alkane thiols is to be derived from U.S. Pat. No. 5,336,812, while EP-A 995 737 proposes the use of alkyl mercaptans with 1 to 12 carbon atoms.

Mixtures containing the desired bisphenol, isomers, intermediates and secondary products of the desired product, as well as unreacted raw materials and water, and the catalyst and cocatalyst used and optionally the reaction products thereof with the components of the reaction system are generally obtained as a result of the reaction of phenols and ketones under the above-mentioned conditions. To obtain bisphenol products of suitable quality for producing high-grade polymer materials, it is necessary to separate these by-products and reaction components as completely as possible from the reaction product bisphenol. For this purpose a combination of various standard purifying operations such as crystallisation, extraction or distillation are usually carried out. Various problems can occur in this process. The bisphenols obtained are thus generally thermally unstable in particular in the presence of catalytically active compounds, acids or bases. This is particularly problematical when using homogeneously distributed acids as catalysts which remain in the product mixture. It is disadvantageous in the neutralization with bases described in EP-A 995 737 or in the extraction of the acids by addition of water proposed in EP-A 679 151 that large quantities of organically loaded waste water are produced by these measures and have to be processed in expensive purification operations. It is also difficult in a procedure of this kind to carry out the reaction continuously with separation of the catalyst. It is also not ensured in a procedure of this type that the sulphur-containing cocatalyst used is also substantially separated from the reaction mixture. Residues of the cocatalyst in the purified bisphenol impair the suitability thereof for producing high-grade polycondensation materials.

A further problem in the production of bisphenols from phenols and in particular from ketones with more than 5 carbon atoms is that the reaction mixtures with high proportions of produced bisphenol can become solid owing to crystallisation of the product, so efficient continuous reaction control and separation of the catalyst is no longer possible. Subsequent melting of the reaction mixture or carrying out the reaction at elevated temperatures to avoid this problem leads to undesired side reactions and reduced selectivities. Reaction control with a high phenol excess or incomplete ketone reaction to avoid a high bisphenol product concentration is disadvantageous, as the space-time yield is thus reduced. Excess phenol and ketone also have to be separated when working up the reaction product. It is proposed in EP-A 995 737 to initially allow phenol and ketone to react in a prereaction until at least 90 mol % of the ketone has reacted and then to add a further quantity of phenol and/or aromatic hydrocarbon to the reaction mixture. A procedure of this type is awkward, does not solve the problem of separating the catalyst and may even introduce a further material into the method which later has to be separated.

The object of the invention is to provide a method for producing bisphenols with acid catalysis in the presence of a sulphur-containing cocatalyst which has a high space-time yield and high selectivity and supplies a product which can be fed to further purification without further expensive processing steps.

DETAILED DESCRIPTION OF THE INVENTION

This object is achieved by a method for producing bisphenols, by reacting phenols or substituted phenols with ketones or diols in the presence of hydrogen chloride and a volatile sulphur compound having an SH bond. The resulting bisphenol is separated from unreacted starting materials and catalysts by distillation.

According to the invention there is no neutralization, in contrast to known methods for producing bisphenol. Moreover, the separation of the product by distillation in the method for producing bisphenols is unknown. The reaction rate may be slowed or the reaction altogether stopped by adding water. Any volatile components such as catalyst, co-catalyst, water and unreacted raw materials having suitably high volatility may be separated from the reaction mixture by distillation.

The reaction rate is much higher than in known methods. The method according to the invention provides high selectivity with high space-time yields. The catalyst and cocatalyst may be substantially separated from the reaction product without cleavage or rearrangement reactions occurring to a noteworthy extent. By isolating and recirculating unreacted ketone the reaction may be carried out with partial ketone conversion with high selectivity, without the reaction mixture becoming solid, having to be diluted or ketone loss occurring.

Starting materials in the method according to the invention are phenol and a large number of phenol derivatives without substituents withdrawing electrons and with unsubstituted 2- and/or 4-position. Suitable phenol derivatives are for example 2-alkylphenols, such as o-cresol, 2-ethylphenol, 2-isopropylphenol or 2-tert.-butylphenol, 2,6-dialkylphenols, such as 2,6-xylinol, 2,6-diethylphenols, 2-methyl-6-i-propylphenol, 2-methyl-6-tert.-butylphenol, 2,6-di-i-propylphenol, 2,6-di-tert.-butylphenol and 2,4-dialkylphenols, such as 2,4-xylenol. Particularly preferably used are phenol or o-cresol. These compounds are, on the one hand, a starting material for the reaction mixture and, on the other hand, a solvent for the reaction mixture.

The further starting materials of the method according to the invention to be reacted with the above-mentioned starting materials are ketones or diols. These ketone or diol components may be cyclic or acyclic aliphatic or aromatic aliphatic ketone compounds. Suitable examples include acetone, butanone, 2-pentanone, 3-pentanone, cyclopentanone, 3-alkylcyclopentanone with an alkyl radical containing 1 to 12 carbon atoms, 3,3-dialkylcyclopentanone with an alkyl radical containing 1 to 12 carbon atoms wherein the alkyl radicals may be identical or different, 3,3,5-trialkylcyclohexanone, wherein the alkyl radicals have 1 to 12 carbon atoms and may be identical or different, cyclohexanone, 3-alkylcyclohexanone with an alkyl radical containing 1 to 12 carbon atoms, 4-alkylcyclohexanone with an alkyl radical containing 1 to 12 carbon atoms, 3,3-dialkylcyclohexanone with alkyl radicals containing 1 to 12 carbon atoms, wherein the alkyl radicals may be identical or different, 3,3,5-trialkylcyclohexanone with alkyl radicals containing 1 to 12 carbon atoms and which may be identical or different, acetophenone. Particularly preferred are cyclohexanones substituted with alkyl radicals, the alkyl radical of which has 1 to 5 carbon atoms. The ketone or diol components may be used in a concentration of 1 to 25 wt. %, preferably 1 to 20 wt. % based on the weight of the reaction mixture.

Suitable catalysts are highly volatile acids, such as concentrated hydrochloric acids and hydrogen chloride gas. Concentrated hydrochloric acid, hydrogen chloride, hydrobromic acid and trifluoroacetic acid are preferred. Volatile sulphur compounds having an SH bond are used as cocatalyst. Compounds of this type include hydrogen sulphide, methyl-, ethyl- and propylmercaptan. Hydrogen sulphide is preferred. The method according to the invention is particularly preferably carried out with hydrogen chloride gas and hydrogen sulphide as catalyst and cocatalyst. The concentration of the catalyst may be 0.3 to 5 wt. %, preferably 0.5 to 2 wt. % based on the weight of the reaction mixture. The concentration of the cocatalyst may be 50 ppm to 1 wt. %, preferably 100 ppm to 0.5 wt. %, based on the weight of the reaction mixture.

At the beginning of the process the starting materials may be placed in the reactor with concentrated acid. The catalyst and cocatalyst are then introduced, preferably while the reaction mixture is stirred. The cocatalyst may also be produced in situ. For this purpose ammonium bisulphide may be introduced into the acid reaction mixture.

The reaction may take place at atmospheric pressure or excess pressure. The reaction is preferably carried out at an excess pressure of 0.1 to 0.5 MPa (1 to 5 bar). The temperature of the reaction mixture may be 10 to 80° C., preferably 25 to 60° C. and particularly preferably 30 to 40° C.

Water is formed during the reaction. This reaction product decelerates the reaction rate, to maintain the rate additional catalyst has to be added. This also applies to the cocatalyst. Catalyst and cocatalyst may be added individually or mixed, in liquid, solid or gaseous form into the reaction mixture. The addition preferably takes place gaseously by blowing into the reaction mixture. The reaction mixture is preferably saturated with respect to catalyst and cocatalyst. The method according to the invention may be carried out continuously or discontinuously, preferably continuously.

The reaction solution may be withdrawn from the lower part of the reactor and conveyed either directly or via a receiver into a distillation device. During distillation, the catalysts, water and unreacted starting materials are separated from the reaction solution.

So that water may be completely evaporated at not too high temperatures, distillation may take place under vacuum and the vacuum may be adjusted in such a way that the base temperature does not lead to product damage. This will be the case at a temperature of 130° C. and lower. At about 130° C. the bisphenols are dissolved and evaporation takes place from the starting compounds such as phenols and cresols only to the extent that a homogeneous solution remains. This procedure allows the virtually complete removal of the water and the catalysts and cocatalysts and supplies a clean, concentrated product solution which may be cleanly and economically crystallised during cooling. The pressure in the distillation column is 50 to 120 mbar, preferably 90 to 110 mbar.

The product withdrawn from the bottom of the column contains, apart from the bisphenol product, phenol and possibly ketone, depending on the boiling point of the product, in amounts of 0 to 15 wt. %, based on the weight of the solution. The product at a temperature of 100 to 130° C. is transferred into a conventional crystallizer. Crystallization preferably takes place in a rotary crystallizer. Depending on the product obtained, recrysallization may take place one to three times, preferably once or twice. With TMC phenols a double crystallization is usually sufficient and with BPA a single crystallization is generally sufficient to obtain a very pure product. The recrystallization preferably takes place with phenol. Difficult to separate mixtures between phenol and other solvents are therefore avoided.

The crystallized product may then also be purified of phenol. The purification may be, for example by thermal desorption of the phenol at raised temperatures while blowing in nitrogen. As temperatures above 190° C. are required in this method, cleavage products are formed. According to a particularly preferred embodiment of the invention the crystallized product is therefore washed with water, and phenol is released in the process from the bisphenol/phenol adducts. The temperature of the water to wash the bisphenol may be 20 to 100° C., preferably 70 to 80° C. The filtered-off cake may be washed with warm water. The removal of phenol from the bisphenol/phenol mixed crystals with water prevents thermal damage to the bisphenol.

The method according to the invention may be carried out in a stirred-tank reactor, a loop reactor or a cascade reactor. Distillation may be continuous or discontinuous distillation. The reaction solution may be introduced into the distillation device between two separation stages with phenol removal with total reflux. The lower part of the distillation device is preferably equipped in such a way that water, catalyst and cocatalyst and optionally the starting material may be removed with phenol vapor.

Bisphenols (diphenols) obtained according to the invention are preferably those of formula (I)

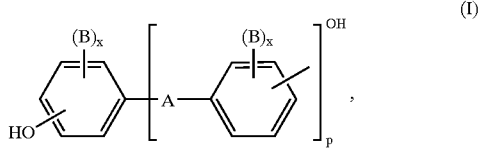

wherein
A is a single bond, $C_1$ to $C_2$-alkylene, $C_2$ to $C_5$-alkylides, $C_5$ to $C_6$-cycloalkylides, —O—, —SO—, —CO—, —S—, —SO$_2$—, $C_6$ to $C_{12}$-aryls on which further aromatic rings optionally containing heteroatoms may be condensed or a radical of formula (II) or (III)

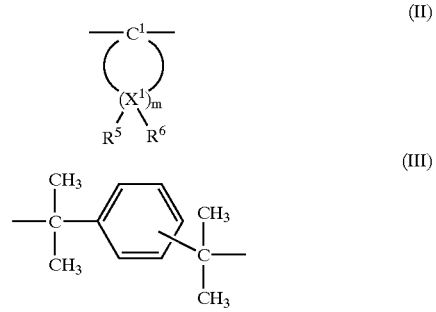

B is $C_1$ to $C_{12}$-alkyl, preferably methyl, halogen, preferably chlorine and/or bromine respectively
x is 0, 1 or 2 respectively independently of one another
p is 1 or 0, and
$R^5$ and $R^6$ for each $X^1$ and independently of one another, represent hydrogen or $C_1$-$C_6$-alkyl, preferably hydrogen, methyl or ethyl,
$X^1$ is carbon and
m is an integer from 4 to 7, preferably 4 or 5 with the proviso, that on at least one atom $X^1$, $R^5$ and $R^6$ are simultaneously alkyl.

Preferred diphenols are hydroquinone, resorcinol, dihydroxydiphenols, bis-(hydroxyphenyl)-$C_1$-$C_5$-alkanes, bis-(hydroxyphenyl)-$C_5$-$C_c$-cycloalkanes, bis-(hydroxyphenyl)-ether, bis-(hydroxyphenyl)-sulphoxides, bis-(hydroxyphenyl)-ketones, bis-(hydroxyphenyl)-sulphones and α,α-bis(hydroxyphenyl)-diisopropylbenzenes) and the derivatives thereof brominated and/or chlorinated in the nucleus.

Particularly preferred diphenols are 4,4'-dihydroxydiphenyl, bisphenol-A, 2,4-bis(4-hydroxyphenyl)-2-methylbutane, 1,1-bis-(4-hydroxyphenyl)-cyclohexane, 1,1-bis-(4-hydroxyphenyl)-3,3,5-trimethylcyclohexane, 4,4'-dihydroxydiphenylsulphide, 4,4'-dihydroxydiphenylsulphone and the di- and tetrabrominated or chlorinated derivatives thereof such as 2,2-bis(3-chloro-4-hydroxyphenyl)-propane, 2,2-bis-(3,5-dichloro-4-hydroxyphenyl)-propane or 2,2-bis-(3,5-dibromo-4-hydroxyphenyl)propane.

The invention will be illustrated, but not limited, by the following examples.

EXAMPLES

Example 1

500 g of reaction solution are placed in a stirred-tank reactor with a volume of 1 l. The reaction solution contains 95.5 wt. % phenol and 4.5 wt. % acetone. At the beginning of the reaction a 5 wt. % aqueous HCl is added. The gas phase is kept at a pressure of 2 bar by HCl gas. 3.3 l/h H$_2$S gas are added to the gas stream. After about 30 minutes, 0.8 l/h reaction solution are continuously pumped into this reactor, the phenol/acetone ratio corresponding to the ratio given above. 0.8 l/h reaction solution are simultaneously pumped from the reactor to the distillation column. The volume in the reactor is controlled in such a way that 30 minutes residence time is reached. The temperature of the reaction mixture is 40° C.

The reaction solution is brought to about 113° C. by a heat exchanger. The vacuum in the distillation column is adjusted to 100 mbar. The reflux ratio is adjusted in such a way that only small amounts of phenol distil off overhead. The base of the column is brought to about 125° C. The volatile substances such as water, hydrogen chloride, hydrogen sulphide and the remainder of the unreacted acetone are condensed and worked up again.

The base of the distillation column then only still contains the reaction products and phenol. The adduct bisphenol/phenol crystallizes from the hot product solution (45° C.). The product is filtered off and washed with warm phenol. The mother liquor may be recycled. The washed adduct is then washed with hot water at a temperature of about 85° C. to separate phenol and bisphenol. The product is vacuum-dried after filtration.

Selectivity in the reaction solution is 95.5% pp BPA and product concentration after drying is 99.71%.

Example 2 (Comparison)

The reaction takes place under the same reaction conditions as in Example 1 but, no H$_2$S was added. The reaction time was doubled. The acetone conversion nevertheless decreases by ⅓, but the selectivity drops to 86.6% pp BPA. The comparison example shows the importance of the cocatalyst for the method according to the invention.

Although the invention has been described in detail in the foregoing for the purpose of illustration, it is to be understood that such detail is solely for that purpose and that variations may be made therein by those skilled in the art without departing from the spirit and scope of the invention except as it may be limited by the claims.

What is claimed is:
1. A method for producing a bisphenol comprising reacting in a reactor a reaction mixture that contains at least one first reactant selected from a first group consisting of phenol and substituted phenols with at least one second reactant selected from a second group consisting of acetone, butanone, 2-pentanone, 3-pentanone, cyclopentanone, 3-alkylcyclopentanone with an alkyl radical containing 1 to 12 carbon atoms, 3,3-dialkylcyclopentanone with an alkyl radical containing 1 to 12 carbon atoms wherein the alkyl radicals may be identical or different, 3,3,5-trialkylcyclohexanone, wherein the alkyl radicals have 1 to 12 carbon atoms and may be identical or different, cyclohexanone, 3-alkylcyclohexanone with an alkyl radical containing 1 to 12 carbon atoms, 4-alkylcyclohexanone with an alkyl radical containing 1 to 12 carbon atoms, 3,3-dialkylcyclohexanone with alkyl radicals containing 1 to 12 carbon atoms, wherein the alkyl radicals may be identical or different, and acetophenone in the presence of hydrogen chloride catalyst and volatile sulphur compound having an SH bond as co-catalyst to obtain a mixture that contains bisphenol, first reactant and second reactant, and separating from the mixture the catalyst and co-catalyst and water of reaction, by distillation to obtain a product containing bisphenol, phenol and crystallizing the product to obtain bisphenol/phenol adduct and then purifying the adduct to exclude phenol by water wash or thermal desorption while blowing in nitrogen to obtain the bisphenol.

2. The method according to claim 1 wherein the catalyst and/or co-catalyst is in liquid or gas state.

3. The method according to claim 2 wherein the co-catalyst in gas state is produced in situ.

4. The method according to claim 1 wherein the concentrations of the catalyst and/or the co-catalyst in the reaction mixture are kept constant at the saturation concentration.

5. The method according to claim 1 wherein the reaction mixture is maintained at 10 to 80° C.

6. The method according to claim 1 wherein the reaction is carried out under pressure.

7. The method according to claim 1 characterized in that it is carried out continuously.

* * * * *